United States Patent
Leise, Jr. et al.

(10) Patent No.: US 6,569,134 B1
(45) Date of Patent: May 27, 2003

(54) REFORMABLE CONVEX ADAPTER FOR OSTOMY APPLIANCE AND METHOD OF USE

(75) Inventors: Walter F. Leise, Jr., Lindenhurst, IL (US); Ronald S. Botten, Gurnee, IL (US); Michael A. Metz, Chicago, IL (US)

(73) Assignee: Hollister Incorporated, Libertyville, IL (US)

( * ) Notice: Subject to any disclaimer, the term of this patent is extended or adjusted under 35 U.S.C. 154(b) by 152 days.

(21) Appl. No.: 09/593,549

(22) Filed: Jun. 14, 2000

(51) Int. Cl.$^7$ .................................................. A61F 5/44
(52) U.S. Cl. ...................... 604/332; 604/336
(58) Field of Search ........................... 604/277, 332–342

(56) References Cited

U.S. PATENT DOCUMENTS

| | | | |
|---|---|---|---|
| 3,898,990 A | * 8/1975 | Nolan | 119/654 |
| 4,213,458 A | 7/1980 | Nolan et al. | 128/283 |
| 4,219,023 A | 8/1980 | Galindo | 128/283 |
| 4,367,732 A | * 1/1983 | Poulsen et al. | 602/56 |
| 4,710,182 A | * 12/1987 | Bryson | 604/339 |
| 4,834,731 A | * 5/1989 | Nowak et al. | 604/339 |
| 5,004,464 A | 4/1991 | Leise | 604/338 |
| 5,147,340 A | 9/1992 | Lavender | 604/344 |
| 5,163,930 A | 11/1992 | Blum | 604/338 |
| 5,167,651 A | * 12/1992 | Leise et al. | 604/339 |
| 5,185,008 A | 2/1993 | Lavender | 604/338 |
| 5,496,296 A | 3/1996 | Holmberg | 604/336 |
| 5,501,678 A | 3/1996 | Olsen | 604/344 |
| 5,607,413 A | 3/1997 | Holmberg et al. | 604/342 |
| 5,609,585 A | * 3/1997 | Botten et al. | 604/332 |
| 5,618,276 A | 4/1997 | Leise et al. | 604/336 |
| 5,730,735 A | 3/1998 | Holmberg et al. | 604/338 |
| 5,811,116 A | 9/1998 | Gilman et al. | 424/443 |
| 5,865,819 A | 2/1999 | Cisko et al. | 604/339 |
| 6,093,276 A | * 7/2000 | Leise et al. | 156/242 |

FOREIGN PATENT DOCUMENTS

EP        0 888 760 A1  *  1/1999

OTHER PUBLICATIONS

EP published appl. 0 888 760 A1.
UK published appl. 2 290 974 A.
UK published appl. 2 277 031 A.

* cited by examiner

*Primary Examiner*—Weilun Lo
*Assistant Examiner*—Linh Truong
(74) *Attorney, Agent, or Firm*—Marshall, Gerstein & Borun

(57) ABSTRACT

A convex adapter for ostomy appliances, including an adapter ring formed entirely of soft, moisture-absorbent, hydrocolloid-containing adhesive material that retains its integrity on hydration and is shape-recoverable, and a thin stretchable cover film (preferably transparent or translucent) removably covering and extending over and beyond the ring's convex bodyside surface. A flexible but substantially non-stretchable release sheet is removably attached to the opposite pouchside surface of the ring and may be peeled away from the ring during an initial step in the use of the product. With the release sheet so removed, a user may grasp adapter ring and its cover film and reform the ring so that its opening is sized and shaped to match a patient's stoma, after which the reformed adapter ring is adhered to the adhesive faceplate of an ostomy appliance, the cover film is removed, and the combination faceplate/adapter is adhesively secured to a patient's peristomal skin surfaces.

12 Claims, 1 Drawing Sheet

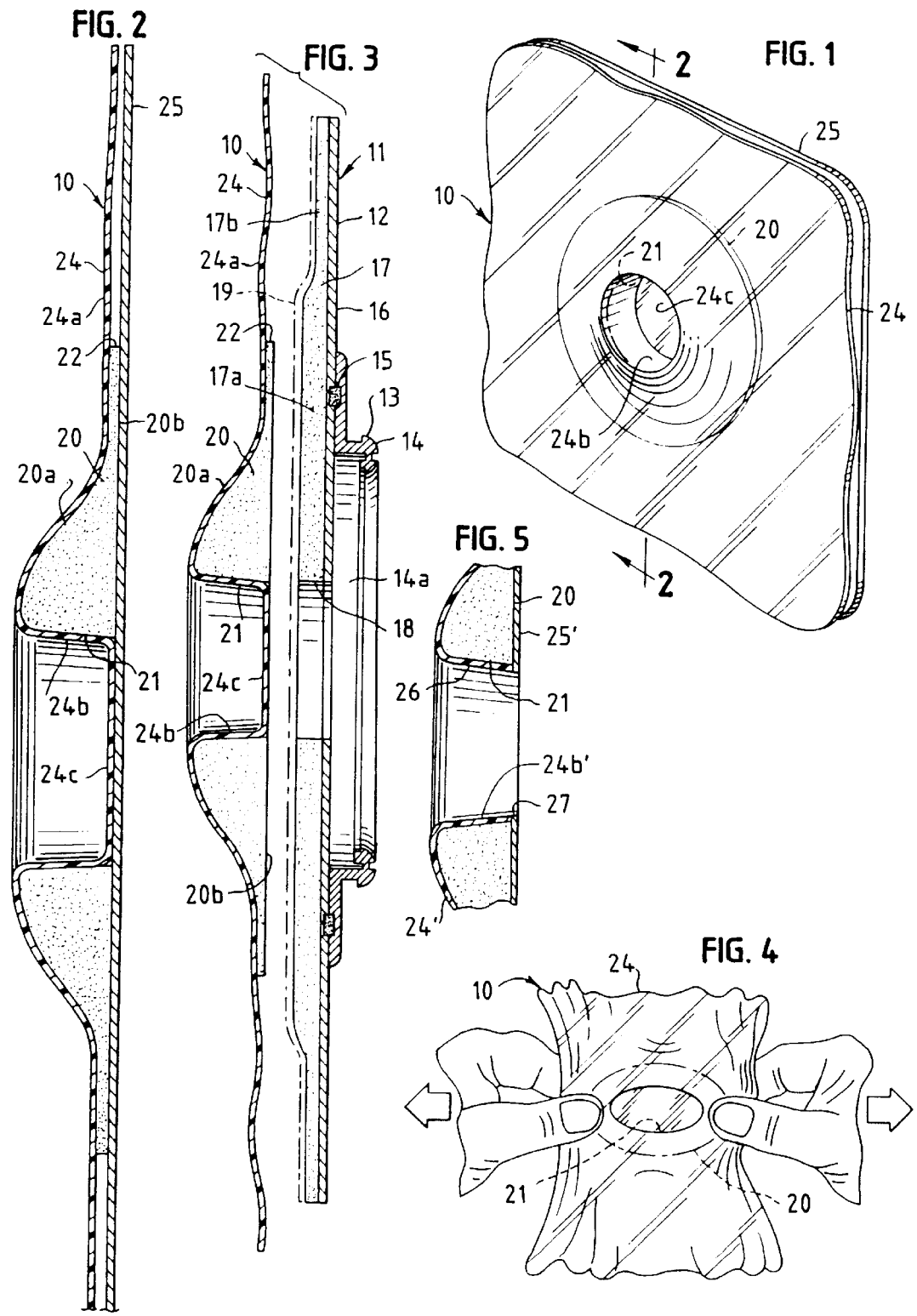

REFORMABLE CONVEX ADAPTER FOR OSTOMY APPLIANCE AND METHOD OF USE

BACKGROUND AND SUMMARY

It has long been known to provide ostomy appliances with relatively rigid convex pressure rings for the purpose of increasing stomal protrusion when such an appliance is worn, thereby aiding in the discharge of effluent directly into the pouch and also prolonging the effectiveness of the adhesive seal between the faceplate and peristomal skin surfaces. Reference may be had to U.S. Pat. Nos. 4,834,731, 5,618,276, 5,607,413, 5,730,735 and 5,501,678 for examples of appliances having such pressure rings. It has also been known to provide rigid convex adapters that may be attached to conventional ostomy faceplates as disclosed, for example, in U.S. Pat. Nos. 4,834,731, 5,004,464, 4,219,023, and 5,163,930.

A premise underlying the design of such convex faceplates and adapters is that a patient's stoma is circular in outline, but studies have shown that is not necessarily the case. In one such study it was noted that stomas not only vary widely in size but that only 58% could be considered circular in shape with 42% being regarded as elliptical or irregular. Nordstrom, G. M. et al, *Local Status of the Urinary Stoma—The Relation to Peristomal Skin Complications*, Scand. J. Urol. Nephrol. 24:117–122 (1990). The possibility that a stoma may be non-circular in shape is also noted in European published application 0 888 760 A1, although that application relates to a planar faceplace rather than a convex one.

Since convexity has been achieved in the past by providing a faceplate or adapter with a relatively stiff plastic element capable of causing stomal protrusion, such a ring has the capability of causing considerable wearer discomfort should the opening of the ring fail to match the shape of a wearer's stoma, or should direct contact between such a ring and a wearer's stoma occur when the wearer bends sharply forward, change positions, or simply moves about.

While it has been known to provide ostomy faceplates with soft, pliant barrier rings, or to supply soft gaskets that may be attached to such rings, such faceplates and gaskets do not function as convex pressure rings. See, for example, U.S. Pat. Nos. 4,213,458 and 4,710,182. Such faceplates/gaskets are commonly formed of a soft flowable material such as karaya, with such material serving as a sealant which flows or is displaced by finger pressure and use into contact with a stoma to prevent leakage and avoid the excorciating effects that may result if stomal effluent contacts peristomal skin surfaces.

The present invention is concerned with a convex adapter that overcomes the shortcomings of prior convex faceplates and adapters and, specifically, one which may be easily and quickly adjusted in size and shape to match the size and shape of a wearer's stoma. The adapter includes a ring formed entirely of moisture-absorbing skin barrier material that is adhesive, soft, rubbery, non-disintegrating upon hydration, non-flowing, and shape-recoverable following compressive deformation. To achieve such objectives, the barrier material should have a continuous phase of an elastomeric adhesive blend including a styrene-olefin-styrene rubber, and a discontinuous phase of hydrocolloid particles dispersed throughout the rubbery adhesive phase.

An important aspect of this invention lies in providing the convex surface of the adapter ring of barrier material with a stretchable cover film that extends outwardly a substantial distance beyond the edges of the ring. The cover film must be removable from the ring and is preferably transparent, or at least translucent, so that the ring's outermost edges, and preferably the opening of a faceplate to which the adapter is to be adhered, may be seen through the film. In addition, the opposite surface of the barrier ring is covered by a removable release sheet which, unlike the cover film, is substantially non-stretchable. The release sheet is preferably of the same size and shape as the cover film, but both should be substantially larger than the faceplate to which the adapter ring is to be attached so as to facilitate removal of the cover film after the faceplate and convex adapter ring have been joined together.

The invention also includes what is believed to be a distinctive method of using the convex adapter. It is well known to provide the adhesive faceplate of an ostomy appliance (either a one-piece appliance or a two-piece appliance) with a small circular starter opening which may then be cut to larger size (with scissors) to match the size and shape of a patient's stoma. Alternatively, the faceplate may be manufactured with an opening sized and shaped (e.g., oval-shaped) to approximate the size and shape of the patient's stoma. In either case, the present method involves reshaping or reforming the adapter ring to match the size and shape of the opening of the faceplate. To that end, a user first strips away the non-stretchable release sheet and then grips the adapter ring, covered only on one side by the stretchable cover film, and reforms the ring by pulling outwardly in opposite directions in the general plane of the ring so that its stoma-receiving opening approximates the size and shape of the faceplate opening. The convex adapter ring is then secured to the faceplate, the cover film is peeled away, and the composite faceplate/adapter is adhesively secured to the patient's peristomal skin surfaces.

Other advantages, features and objects of the invention will become apparent from the specification and drawings.

DRAWINGS

FIG. 1 is a perspective view of a convex adapter as it would be supplied to a user.

FIG. 2 is an enlarged sectional view taken along line 2—2 of FIG. 1.

FIG. 3 is a sectional view similar to FIG. 2 but showing the adapter with its release sheet removed and with the adapter located in proximity to the faceplate of an ostomy appliance (the release sheet of the faceplate also having been removed).

FIG. 4 is an elevational view showing the step of reforming the adapter so that its stoma-receiving opening becomes oval-shaped.

FIG. 5 is a fragmentary sectional view showing a second embodiment in which the cover film and release sheet are cut to provide an opening in register with the stoma-receiving opening of the convex barrier ring.

DETAILED DESCRIPTION OF PREFERRED EMBODIMENTS

Referring to FIGS. 1–4, the numeral 10 generally designates a convex adapter for use with an adhesive faceplate 11 (FIG. 3) of an ostomy appliance. A protective sheet 19 formed of silicone-coated paper or other suitable sheet material, shown only in phantom in FIG. 3, covers the bodyside surface of the adhesive layer and is removable from that surface at the time the faceplate is being prepared for use. In the particular construction illustrated in FIG. 3, appliance 11 is a two-piece appliance in which only the adhesive faceplate component 12 of the appliance is depicted. The faceplate includes a coupling ring 13 of flexible plastic material similar in construction and operation to the male coupling component disclosed in co-owned U.S. Pat. No. 5,185,008, the disclosure of which is incorporated by reference herein. The ring includes a male element 14 adapted to be received in the channel of a mating coupling ring attached to a collection pouch (not shown). The faceplate ring 13 is joined by heat seal 15 to the thermoplastic film 16 of faceplate 12, and a layer 17 of a skinfriendly pressure-sensitive adhesive 17 is secured to the bodyside surface of film 16. The adhesive layer 17 and film 16 have a central opening 18 that is generally concentric with the opening 14a of coupling ring 13.

Opening 18 may be relatively small and serve only as a starter opening that may be cut (with scissors) to match the size and shape of a patient's stoma. Thus, if a stoma is of flattened oval or ellipical shape, a caregiver or patient may enlarge opening 18 so that it matches the outline of the stoma. Alternatively, opening 18 may be precut and presized during manufacture to approximate the size and shape (e.g., oval) of a wearer, it being understood that in such a case the manufacturer would offer a line of faceplates having openings of different sizes and shapes.

The adhesive layer 17 may be formed of any suitable pressure-sensitive adhesive commonly used for securing the faceplates of ostomy appliances to the peristomal skin surfaces of a wearer. For example, a hypoallergenic medical-grade acrylic adhesive may be used. However, it is preferable that the adhesive layer be formed of soft, skinfriendly hydrocolloid-containing adhesive material that is capable of absorbing moisture and has both wet and dry tack. Such a material is commonly referred to as a skin barrier composition and typically comprises a continuous elastomeric adhesive phase having hydrocolloid particles dispersed throughout the continuous phase. Initial tack, usually referred to as "dry tack," is provided by the continuous phase but, because such a composition is occlusive or non-breathable, adherence to the skin would be disrupted by perspiration and by liquid stomal discharge if it were not for the dispersed hydrocolloids which absorb fluids and thereby maintain and possibly enhance adhesive attachment to the skin. U.S. Pat. No. 4,551,490 and other references disclose that suitable water-absorbing and swellable hydrocolloid gums may include sodium carboxymethylcellulose, pectin, gelatin, guar gum, locust bean gum, and the like. The elastomers used in the continuous phase may be polyisobutylene, natural rubber, silicone rubber, acrylonitrile rubber and other elastomers known in the art to have similar properties. In the particular faceplate depicted in FIG. 3, the adhesive layer 17 is contoured, having a relatively thick annular inner portion 17a and a thin outer portion 17b although, if desired, layer 17 may instead be of substantially uniform thickness throughout. A protective sheet 19 formed of silicone-coated paper or other suitable sheet material, shown only in phantom in FIG. 3, covers the bodyside surface of the adhesive layer and is removable from that surface at the time the faceplate is being prepared for use.

In outline, faceplate 12 may be of generally rectangular (square) shape with rounded corners as depicted, for example, in co-owned U.S. Pat. Nos. 5,147,340 and 5,167,651, but other shapes such as circular, oval, or even triangular (see, for example, U.S. Pat. No. 5,811,116) may be provided.

Adapter 10 comprises an adapter ring 20 having a convex bodyside surface 20a and a generally planar pouchside surface 20b. A stoma-receiving opening 21 of generally cylindrical shape extends through the ring. The ring's outermost edge 22 is circular and concentric with stoma-receiving opening 21.

The adapter ring 20 is formed entirely of soft skin barrier material that is generally non-flowable, retains its integrity upon hydration, and has shape-recovering properties. It should also be compatible, at least for the expected duration of usage, with the adhesive composition 17 of faceplate 12. If the faceplate adhesive 17 is composed of a hydrocolloid-containing skin barrier material, adapter ring 20 may be of similar or identical composition as long as the composition of the ring is flow-resistant, does not disintegrate as it absorbs moisture, and is generally shape-recoverable following compressive deformation.

More specifically, the adapter ring 20 should be of a composition consisting essentially of a continuous phase of two or more elastomeric adhesives and a discontinuous phase of hydrocolloid particles dispersed throughout the continuous phase. For flow resistance, shape-recoverability, and the capacity to retain integrity during swelling of the hydrocolloid component upon liquid absorption, the continuous phase includes a physically crosslinked elastomer such as a styrene-olefin-styrene block copolymer as disclosed in co-owned U.S. Pat. No. 5,492,943, the disclosure of which is incorporated by reference herein. The composition of that patent includes a blend of two viscoelastic adhesive elastomers, specifically high molecular weight polyisobutylene and a styrene block copolymer which, along with a plasticizer (preferably petrolatum) and a suitable tackifier and antioxidant, form a continuous phase in which hyrocolloid particles such as sodium carboxymethylcellulose and pectin are dispersed. While the composition of the aforementioned patent is preferred, it is believed that other adhesive barrier compositions containing physically crosslinked elastomers or mixtures of such elastomers, such as those disclosed in U.S. Pat. Nos. 4,231,369, and 4,551,490, might also be used.

The importance of including a styrene-olefin-styrene block copolymer in the blend of materials of the barrier's adhesive phase lies in providing a rubbery constituent that contributes to the barrier material's integrity upon hydration, its non-flowability, resistance to compressive deformation, and recoverability following such deformation. At the same time, the barrier material is of sufficient softness and low modulus that pulling forces may be applied by the fingers in opposite directions (in the general plane of the ring) to reform the outline of barrier layer 17 and the shape of the stoma opening extending therethrough, assuming that release sheet 25 has first been removed as described hereinafter.

Preferably, the viscoelastic adhesive phase is a blend of elastomers composed of about 2 to 15% (preferably 3 to 7%) by weight of one or more high molecular weight polyisobutylenes and about 5 to 20% by weight (preferably 17 to 14%) of one or more styrene block copolymers. "High molecular weight" here refers to a polyisobutylene having a viscosity average molecular weight within the range of about 75,000 to 2,350,000 (preferably about 1,000,000 to 1,900,000) as determined from intrinsic viscosity measurements in diisobutylene at 20° C. Such polyisobutylenes are commonly available and are known, for example, under the designations Vistanex MM-L80, MM-L100, MM-L120, and MM-L140 from Exxon Corp., Houston, Tex.

Styrene block copolymer or copolymers suitable for blending with such high molecular weight polyisobutylene (s) may be identified generally as styrene-olefin-styrene block copolymers. Particularly suitable for this purpose are styrene-isoprene-styrene and styrene-butadiene-styrene block copolymers, both of which are commercially available, for example, from Shell Chemical and other suppliers. A styrene-isoprene-styrene block copolymer marketed as Kraton 1107 (Shell Chemical) is believed particularly suitable, but other Kraton copolymers, such as Kraton 1100, 1101, and 1102 are also considered suitable.

Petrolatum may be used advantageously as a hydrocarbon plasticizer component in the adhesive barrier composition, although mineral oil may also be used. In addition, the composition may contain one or more hydrocarbon tackifier resins, such as the aliphatic hydrocarbon resin tackifier commercially available from Hercules Inc. (Wilmington, Del.) as Piccotac 95. Other tackifiers such as trimethylol propane esters of rosin (Staybelite Ester 10 from Hercules) or pentacrythritol esters of rosin (Pentalyn H from Hercules) might also be used. In addition, the barrier composition may include a suitable antioxidant such as Irganox 1010 or Irganox 1076 (Ciba Geigy) or any of a number of other commercially-available antioxidants.

As shown in FIGS. 1 and 2, a flexible cover film 24 covers the convex surface of barrier ring 20 and includes an outer portion 24a that extends outwardly a substantial distance beyond the peripheral edge 22 of ring 20. Film 24 is shown to be generally square in outline, with rounded corners, but other shapes may be provided. What is important is that the thermoplastic cover film 24 be thin and easily stretchable so that deforming forces may be applied to the adapter (as hereinafter described) without objectionable resistance being presented by the cover film. It is also important that the film be removable from the convex surface 20a of the barrier ring 20 and that it be sufficiently transparent or translucent to allow the outermost edge 22 and preferably the opening of a faceplate to which the adapter is to be adhered, to be viewed therethrough.

In the embodiment illustrated in FIGS. 1–4, cover film 24 extends into the opening 21 of barrier ring 20, having a generally cylindrical sleeve portion 24b that extends axially and covers the cylindrical surface of the ring as well as an end portion 24c that bridges the barrier opening along the faceplate-facing end of that opening.

Any of a variety of thin, highly-flexible thermoplastic elastomers may be used for stretchable cover film 24. It is believed that polyurethane elastoplastics marketed under the designation "Estane" by B.F. Goodrich Chemical, and copolyether-ester thermoplastics marketed under the designation "Hytrel" by DuPont are particularly suitable, but other materials having similar properties may be used.

The pouchside surface 20b of the adapter ring 20 is covered by a removable release sheet 25 that, unlike film 24, is relatively stiff and non-stretchable. Siliconized paper may be used with the silicone-treated surface being in contact with the ring surface 20b to facilitate removal of the sheet at the time of application. Alternatively, the release sheet 25 may be composed of a polymeric material such as, for example, silicone-coated polyethylene terephthalate.

While both the release sheet 25 and the cover film 24 should adhere only weakly to the adhesive adapter ring 20, the forces of adhesion between the cover film and the ring should be greater than those between the ring and the release sheet, thereby permitting a user to peel the release sheet away from the pouchside surface of the adapter ring 20 without risking detachment of the adapter ring from its cover film. Similarly, the forces of adhesion between the adapter ring 20 and the adhesive layer 17 of faceplate 12 should be substantially greater than the forces of adhesion between cover film 24 and the contoured surface of adapter ring 20, thereby permitting the cover film to be peeled away from the adapter ring after that ring has been secured to the faceplate.

The release sheet 25 and cover film 24 are of the same size and shape and have their edges in register, having been cut simultaneously in the same cutting step of a manufacturing procedure that may be of the type described in co-owned U.S. Pat. No. 5,716,475. Thus, if cover film 24 is of generally rectangular shape as shown in FIG. 1, the coextensive release sheet 25 is of the same shape. In that connection, it should be noted that both the release sheet and the cover film are substantially larger than faceplate 12, thereby facilitating removal of the cover film after the adapter ring 20 and faceplate 12 are secured together. Also, it will be observed that in the preferred embodiment depicted in the drawings, the portion 24c of the cover film disposed within the opening 21 of the adapter ring 20 is in contact with, or in close proximity to, release sheet 25. The cover film thereby defines a generally cylindrical cavity into which a user may insert the tips of one or both fingers when reshaping of the adapter for attachment to a faceplate is desired.

In use of the invention, if the faceplate is of the type having a small starter opening, then a first step would involve enlarging that opening with scissors so that it matches the size and irregular (e.g., oval) shape of the patient's stoma. Thereafter, the protective release sheet 19 is peeled away from the adhesive surface of the faceplate and the release sheet 25 of adapter 10 is similarly removed. The user then grips the adapter ring 20 and its cover film 24 as shown in FIG. 4 and reforms the soft and deformable ring so that the stoma-receiving opening of the ring is of essentially the same size and shape as the opening of the faceplate. For example, if the larger faceplate opening is of oval shape, then opposite sides of the film-backed adapter ring 20 are pulled outwardly until opening 21 is also of oval shape and closely approximates the size and shape of the faceplate opening. The two openings are then brought into alignment, with the transparency of the stretchable cover film 24 facilitating such alignment, and the pouchside surface 20b of the adapter ring is secured to the exposed surface of adhesive layer 17 of faceplate 12. With the convex adapter secured to the faceplate, the user then peels away cover film 24 and secures the faceplate with its convex adapter in place to the skin surfaces surrounding the stoma.

The embodiment of FIG. 5 is similar to the one already described except that neither the cover film 24' nor the release sheet 25' bridges the opening 21 of adapter ring 20. Instead, aligned openings 26 and 27 are provided in cover film 24' and release sheet 25', respectively. The absence of film portion 24c of the previous embodiment may be advantageous to the extent that the cover film may impose even less resistance to reshaping of the adapter ring so that its opening 21 is brought into conformity with the size and shape of the patient's stoma. In both embodiments, if stretching and reshaping involves insertion of the finger tips into the opening of the adapter, finger contact with the sticky adhesive material of the adapter ring is avoided because of the protective sleeve 24b and 24b' of the cover film that lines the wall of barrier opening 21.

While in the foregoing we have disclosed embodiments of the invention in considerable detail for purposes of illustration, it will be understood by those skilled in the art that many of these details may be varied without departing from the spirit and scope of the invention.

What is claimed is:

1. A convex adapter for use with an adhesive faceplate of an ostomy appliance, comprising an adapter ring formed entirely of soft shape-recoverable skin barrier material having a convex body surface, a generally planar opposing surface, and a centrally-located stoma-receiving opening therethrough; a removable release sheet covering said opposing surface; and a stretchable and removable cover film covering said convex surface; said barrier material consisting essentially of a continuous phase of an elastomeric adhesive and a discontinuous phase of moisture-absorbing and swellable hydrocolloid particles dispersed therein; said removable cover film being sufficiently transparent for revealing said adapter ring therethrough and having a marginal portion extending outwardly beyond the periphery of said adapter ring.

2. The convex adapter of claim 1 in which said removable release sheet has a marginal portion extending outwardly beyond the periphery of said adapter ring.

3. The convex adapter of claim 2 in which said removable cover film and said removable release sheet are of substantially the same size.

4. The convex adapter of claim 1 in which said removable cover film has an outline larger than that of an adhesive faceplate to which said ring is adapted to be secured.

5. The convex adapter of claims 1, 2 or 3 in which said barrier material consists essentially of a continuous phase of an elastomeric adhesive having a styrene-olefin-styrene copolymer as an ingredient thereof.

6. The convex adapter of claim 5 in which said barrier material is a homogenous blend of a styrene-olefin-styrene copolymer and polyisobutylene for providing said adapter ring with shape recoverability, non-flowability, and retention of integrity on hydration.

7. The convex adapter of claims 1, 2 or 3 in which said cover film extends into said centrally-located stoma-receiving opening of said adapter ring; said stoma-receiving opening having a generally cylindrical surface covered by said cover film.

8. The convex adapter of claim 7 in which said cover film bridges said stoma-receiving opening along the plane of said opposing surface of said adapter ring.

9. The convex adapter of claims 1, 2 or 3 in which said skin barrier material of said adapter ring adheres more strongly to said removable cover film than to said release sheet.

10. A method for providing an adhesive faceplate of an ostomy appliance with a convex adapter having an opening reformable to match the shape of a patient's stoma, comprising the steps of providing an adapter ring composed of soft, shape-recoverable adhesive skin barrier material having a convex surface covered by a stretchable and removable cover film; said cover film being generally transparent and having an outer portion extending substantially beyond the periphery of said adapter ring; gripping portions of said cover film and adapter ring and urging the same in different directions with sufficient force to alter the shape of said opening of said adapter ring so that it matches the outline of a patient's stoma; securing said adapter ring to the bodyside surface of an adhesive faceplate of an ostomy appliance while the opening of said ring is so altered in shape; and then removing said cover film from said adapter ring and said faceplate.

11. The method of claim 10 in which said cover film is larger than said adhesive faceplate and includes a marginal portion extending beyond said faceplate when said adapter ring is secured thereto; said removing step comprising gripping a portion of said cover film extending beyond said faceplate and peeling said cover film away from said adapter ring and faceplate.

12. The method of claims 10 or 11 in which said adapter ring includes a stoma-receiving opening having a generally cylindrical surface and said cover film extends into said opening and covers said surface; said step or urging said cover film and adapter ring in different directions comprises contacting opposing portions of said film-covered cylindrical surface of said ring and urging the same outwardly in opposite directions.

* * * * *